US008240200B2

(12) United States Patent
Chocron et al.

(10) Patent No.: US 8,240,200 B2
(45) Date of Patent: Aug. 14, 2012

(54) TECHNIQUES TO MEASURE STRAIN DEVELOPMENT AND FAILURE IN A FABRIC

(75) Inventors: Isaias S. Chocron, San Antonio, TX (US); Arthur E. Nicholls, Helotes, TX (US); Charles E. Anderson, Jr., San Antonio, TX (US); James D. Walker, San Antonio, TX (US)

(73) Assignee: Southwest Research Institute, San Antonio, TX (US)

(*) Notice: Subject to any disclaimer, the term of this patent is extended or adjusted under 35 U.S.C. 154(b) by 136 days.

(21) Appl. No.: 12/548,812

(22) Filed: Aug. 27, 2009

(65) Prior Publication Data
US 2011/0048123 A1     Mar. 3, 2011

(51) Int. Cl.
*G01L 5/04* (2006.01)
(52) U.S. Cl. ............. 73/159; 73/12.01; 73/570; 73/584; 73/587; 73/645; 73/647
(58) Field of Classification Search ................. 73/12.01, 73/35.14, 788, 862; 428/911; 2/2.5
See application file for complete search history.

(56) References Cited

U.S. PATENT DOCUMENTS

| | | | | | |
|---|---|---|---|---|---|
| 2,316,975 | A | * | 4/1943 | Ruge | 33/788 |
| 4,715,235 | A | * | 12/1987 | Fukui et al. | 73/862.68 |
| 6,277,771 | B1 | * | 8/2001 | Nishimura et al. | 442/229 |
| 2005/0274168 | A1 | * | 12/2005 | Stuetzler | 73/12.01 |
| 2006/0053534 | A1 | * | 3/2006 | Mullen | 2/456 |
| 2006/0258247 | A1 | * | 11/2006 | Tao et al. | 442/301 |
| 2007/0171024 | A1 | * | 7/2007 | Yang et al. | 338/2 |

OTHER PUBLICATIONS

Author: Unknown, Title: Practical Strain Gauge Measurements, Publisher: Agilent Technologies, pp. E-94 to E-130, Date Accessed Page Available on Web Site: Oct. 15, 2006, Access Availability Source: http://replay.web.archive.org/20061015194212/http://www.omega.com/techref/pdf/StrainGage_Measurement.pdf Date Accessed: May 2, 2011.*
Author: Unknown, Title: Practical Strain Gauge Measurements, Publisher: Agilent Technologies, pp. E-94 to E-130, Date Accessed Page Available on Web Site: Oct. 15, 2006, Access Availability Source: http://replay.web.archive.org/20061015194212/http://www.omega.com/techref/pdf/StrainGage_Measurement. pdf Date Accessed: May 2, 2011.*

(Continued)

*Primary Examiner* — Lisa Caputo
*Assistant Examiner* — Roger Hernandez-Prewitt
(74) *Attorney, Agent, or Firm* — Grossman, Tucker, Perreault + Pfleger, PLC

(57) ABSTRACT

The present disclosure relates to a system and method for characterizing an impact in a fabric. The system may include a sensing element woven in the fabric wherein a parameter of the sensing element depends on a strain in the sensing element; a transducer coupled to the sensing element wherein the transducer is configured to generate an output based on the parameter of the sensing element; and a controller coupled to the transducer, the controller configured to receive the output of the transducer, to determine a strain in the sensing element based, at least in part, on a change in the output of the transducer, and to characterize the impact in the fabric based on the strain in the sensing element.

29 Claims, 10 Drawing Sheets

OTHER PUBLICATIONS

Chocron, et al., "Experimental Determination of Strain in Fabrics under Ballistic Impact," Southwest International Symposium on Ballistics, New Orleans, LA, Sep. 20-26, 2008, pp. 984-991.

Chocron, et al., "Measurement of strain in fabrics under ballistic impact using embedded nichrome wires, part I: Technique," International Journal of Impact Engineering 36 (2009) pp. 1296-1302.

Chocron, et al., "Measurement of strain in fabrics under ballistic impact using embedded nichrome wires, part II: Results and analysis," International Journal of Impact Engineering (2009) pp. 1-13.

Tabiei, et al., "Ballistic Impact of Dry Woven Fabric Composites: a Review," Applied Mechanics Reviews, Jan. 2008, vol. 61; pp. 010801-1-010801-13 (13 pages).

* cited by examiner

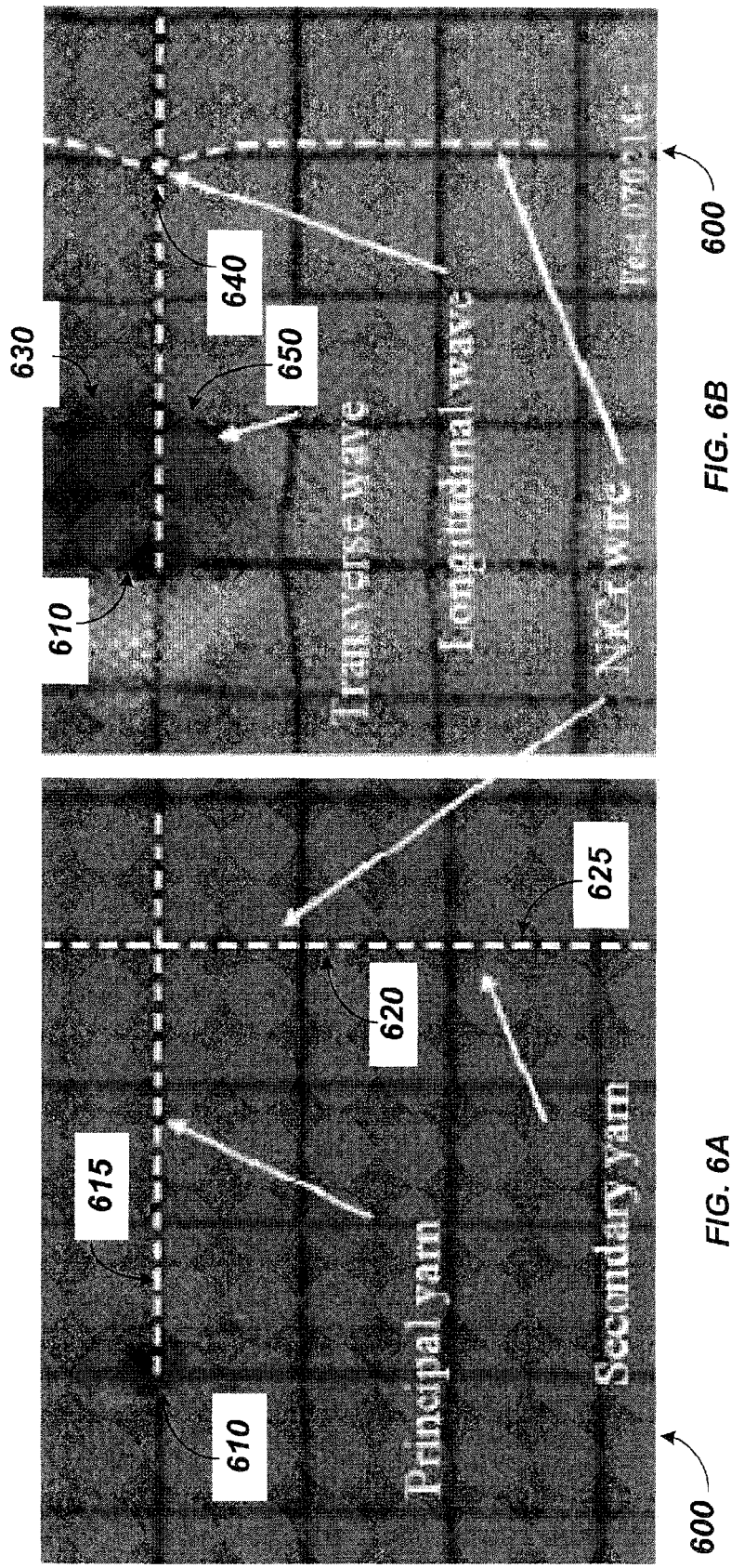

TECHNIQUES TO MEASURE STRAIN DEVELOPMENT AND FAILURE IN A FABRIC

FIELD OF THE INVENTION

This disclosure relates to a system, method and article configured for determining strain development and failure in a fabric.

BACKGROUND

Fabrics may be used in protective clothing such as bulletproof or bullet-resistant vests. The fabrics may be configured to absorb and/or distribute the impact of a projectile. Such fabric may include one or more layers. Each layer may include a plurality of yarns woven together. Each yarn may include a plurality of aramid and/or para-aramid fibers such as KEVLAR by E. I. du Pont de Nemours and Company or TWARON by Teijin Aramid. An aramid fiber may be understood as an aromatic polyamide whose chain molecules are highly oriented along a fiber axis. Para-aramids may have relatively much higher tenacity and elastic modulus than aramids and may provide outstanding strength to weight properties.

A fabric and yarns in the fabric subjected to ballistic impact may experience strains that depend on the ballistic impact. In a yarn, strain may be understood as a relative change in length. For example, the strain experienced by a particular yarn may depend, at least in part, on the location and/or orientation of the yarn relative to a point of ballistic impact as well as a travel direction, velocity and/or type of a ballistic projectile. It may therefore be desirable to detect strains in one or more yarns in a fabric subject to ballistic impact.

SUMMARY

The present disclosure relates in one embodiment to a system for characterizing an impact in a fabric. The system includes a sensing element woven in the fabric wherein a parameter of the sensing element depends on a strain in the sensing element; a transducer coupled to the sensing element wherein the transducer is configured to generate an output based on the parameter of the sensing element; and a controller coupled to the transducer, the controller configured to receive the output of the transducer, to determine a strain in the sensing element based, at least in part, on a change in the output of the transducer, and to characterize the impact in the fabric based on the strain in the sensing element.

The present disclosure relates in another embodiment to a method for characterizing an impact in a fabric. The method includes providing a sensing element in the fabric wherein the sensing element is woven in the fabric; monitoring an output, the output based on a parameter of the sensing element wherein the parameter of the sensing element depends on a strain in the sensing element; detecting a change in the output; determining a strain in the sensing element based on the change in the output; and characterizing the impact on the fabric based on the strain in the sensing element.

In yet another embodiment, the present disclosure relates to an article comprising a storage medium having stored thereon instructions that when executed by a machine result in the following operations: monitoring an output, the output based on a parameter of a sensing element wherein the sensing element is woven in a fabric and the parameter of the sensing element depends on a strain in the sensing element; detecting a change in the output; determining a strain in the sensing element based on the change in the output; and characterizing the impact in the fabric based on the strain in said sensing element.

BRIEF DESCRIPTION OF THE DRAWINGS

The detailed description below may be better understood with reference to the accompanying figures which are provided for illustrative purposes and are not to be considered as limiting any aspect of the invention.

FIGS. 6A and 6B depict an exemplary fabric at impact and 15 μs after impact, respectively.

DETAILED DESCRIPTION

In general, the present disclosure describes a system and method that may be used to characterize an impact in a fabric. The fabric may include one or more layers of woven yarns and may be instrumented with one or more sensing elements distributed in the fabric. Each sensing element may be configured for detecting strain in the fabric as a result of a ballistic impact. For example, a parameter of a sensing element may change based on a strain in the sensing element. The strains may be detected as a function of time. A ballistic impact may be an impact by a projectile moving at a velocity. Characterizing the impact in the fabric may include determining a characteristic of the ballistic impact and/or a status of the fabric during the ballistic impact. For example, characteristics of the ballistic impact may include a location of the impact in the fabric and/or speed and/or direction of an impacting projectile. Status of the fabric may include diagnostics of a layer, e.g., strain in a yarn during impact, speed of strain waves in the fabric, whether a yarn has broken, whether one or more layers have failed, i.e., have been penetrated, and if a layer has failed, how long it took to fail. In some embodiments the detected strains may be used to verify and/or validate models of fabrics subjected to a ballistic impact.

For example, each sensing element may be a Nickel-Chromium resistance (NiCr) wire. NiCr is a relatively high resistivity wire that is commonly used in heating elements and the like. Preferably, the NiCr wire may be 40 gage (diameter of about 0.00285 in. or 0.07239 mm). The 40 gage NiCr wire may have a nominal density of about 8.4 g/cm$^3$ and an elastic modulus of about 220 GPa (~31.9 million psi). A resistance of a NiCr wire may change with strain in the wire. Resistance may then be the sensing element parameter monitored. Resistance of a NiCr wire may be detected and, based on the detected resistance, strain in the NiCr wire may be determined. For example, the resistance of a NiCr wire sensing element may be detected using a Wheatstone bridge. This detection method is discussed in more detail below.

Figure 1:
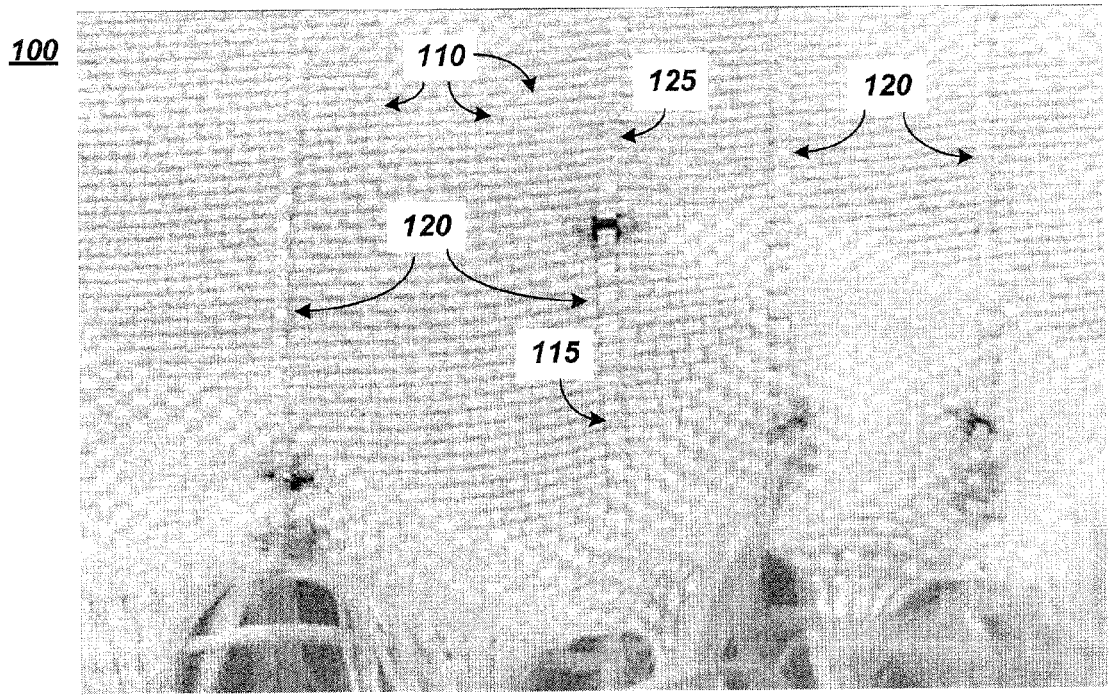
FIG. 1 depicts a fabric including sensing elements consistent with the present disclosure.

Attention is directed to FIG. 1 which depicts a portion of a fabric 100. The fabric 100 may include a plurality 110 of individual yarns 115 that have been woven into layers and the layers may be combined together to form the fabric 100. Each yarn 115 may include a para-aramid fiber. An aramid fiber may be understood as an aromatic polyamide whose chain molecules are oriented along a fiber axis. Para-aramids may have relatively much higher tenacity and elastic modulus than aramids and may provide outstanding strength to weight properties. For example, the para-aramid fiber may include KEVLAR™ available from E.I. du Pont de Nemours and Company. In another example, the para-aramid fiber may include TWARON™ available from Teijin Aramid.

The fabrics herein which may therefore be preferably utilized for a ballistic application include those fabrics that may provide a tensile strength of equal to or greater than about 3.45 GPa (~500,000 psi) and a tensile modulus of about 75 GPa to 200 GPa (~10 million psi to ~30 million psi). Such fabrics may therefore include those polymers which are generally known as lyotropic liquid crystalline polymers as well as other polymers that are capable of relatively high degrees of chain orientation (e.g., greater than or equal to 50% or in the range of 50-100%) and associated mechanical strength. The fabric 100 may include a plurality 120 of sensing elements, e.g., NiCr resistance wire 125. Each NiCr wire 125 may be woven into the fabric 100 by replacing a yarn 115 with the yarn 115 plus a NiCr wire 125. For example, the wire 125 may be juxtaposed with the yarn 115 and may follow a crimp of the yarn 115. Reference to being woven may be understood as that situation where the sensing element (e.g., the NiCr wire) is interlaced into the fabric.

In general, the fabric herein may include a plurality of layers of woven yarns. Each layer may include a plurality of sensing elements, e.g., NiCr wires. Accordingly, the fabric may include an array of NiCr wires in each layer and the plurality of layers may form a three-dimensional matrix of sensing elements. A position of a NiCr wire may be defined by a layer number and a two-dimensional position or position and orientation within the layer. In FIG. 1, each one of the plurality 120 of NiCr wires is shown with a long axis substantially parallel to a long axis of each other of the plurality 120 of NiCr wires. It is contemplated that, in some embodiments, a plurality of NiCr wires may be arranged so that a first subset of NiCr wires crosses a second subset of NiCr wires. A NiCr wire in the first subset may be substantially parallel to other NiCr wires in the first subset and substantially perpendicular to NiCr wires in the second subset. In this configuration, each NiCr wire may include an insulating, nonconductive coating to reduce the likelihood of crossed NiCr wires shorting one another.

Based on detection and analysis of strains in the plurality 120 of NiCr wires, and with knowledge of the general placement and/or orientation of each NiCr wire in a layer and each layer in the fabric 100, a characteristic of a ballistic impact and/or a status of the fabric 100 may be determined.

Figure 2:
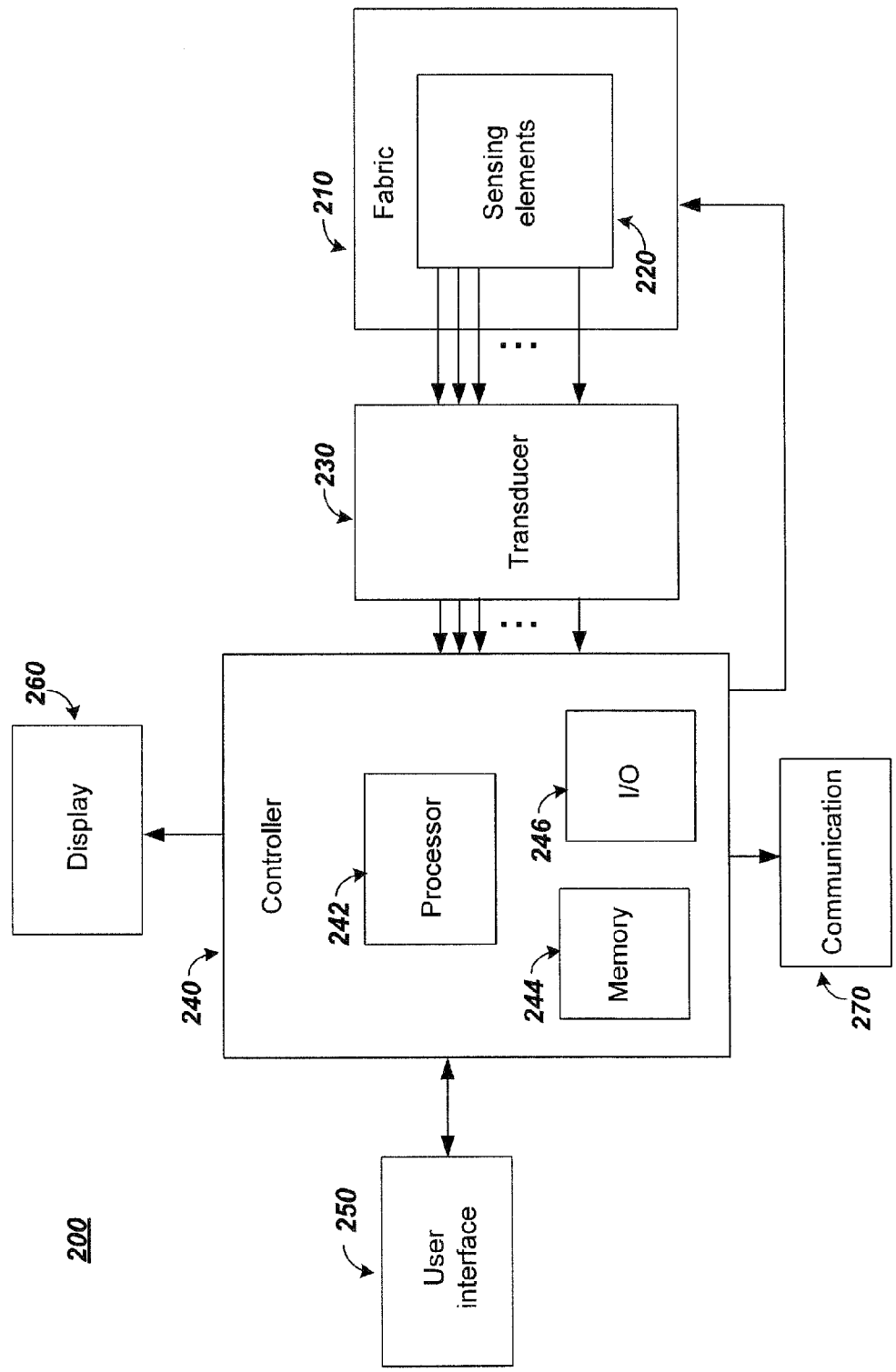
FIG. 2 depicts an exemplary system block diagram consistent with the present disclosure.

Attention is directed to FIG. 2 which depicts a functional block diagram of a system 200 for sensing strain in a fabric consistent with the present disclosure. The system 200 may include a fabric 210. The fabric 210 may include a plurality 220 of sensing elements. For example, each sensing element may be a NiCr wire. The plurality 220 of NiCr wires may be coupled to a transducer 230. The transducer 230 may be configured to detect a resistance of one or more of the plurality 220 of NiCr wires and to provide an output based on the detected resistance. The transducer 230 may include a plurality of channels where each channel may correspond to one of the plurality 220 of NiCr wires. For example, each channel may include a full Wheatstone bridge. In this example, the transducer 230 may include a number of Wheatstone bridges equal to the number of NiCr wires. In another example, the transducer 230 may include a multiplexer coupled between each NiCr wire and a full Wheatstone bridge. In this example, the transducer 230 may include fewer full Wheatstone bridges than the number of NiCr wires. A particular configuration may depend on a rate of change of strain in a NiCr wire due to a ballistic impact.

Figure 3:
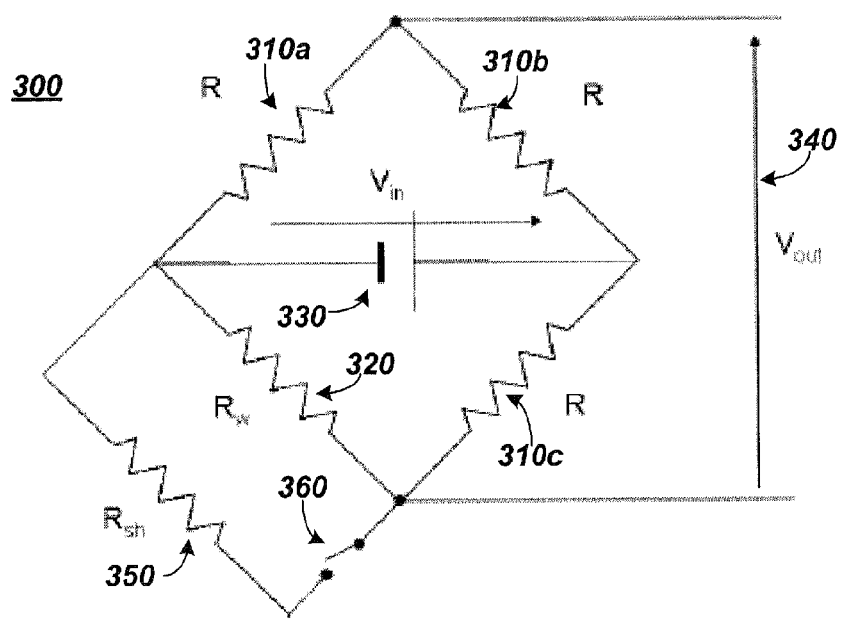
FIG. 3 depicts an exemplary Wheatstone bridge circuit consistent with the present disclosure.

FIG. 3 depicts an example of a full Wheatstone bridge 300. The full Wheatstone bridge 300 may be used to detect changes in a resistance with relatively high resolution. The bridge 300 includes three resistors 310a, 310b, 310c coupled as a first, second and third branch, respectively, of the bridge 300. In an embodiment, each of the resistors 310a, 310b, 310c may have a resistance R. For example, resistance R may be nominally 120 ohms. A NiCr wire 320 may be coupled as a fourth branch of the bridge 300. For example, the NiCr wire 320 may have a nominal resistance of 121 ohms. In some embodiments, a shunt resistor $R_{sh}$ 350 may be controllably coupled in parallel with the NiCr wire 320 in the fourth branch of the Wheatstone bridge 300. For example, the shunt resistor $R_{sh}$ 350 may be coupled in parallel with the NiCr wire 320 by a switch 360. For example, the shunt resistor $R_{sh}$ 350 may be a precision resistor with a nominal resistance of 5 kilo-ohms.

An input voltage $V_{in}$ 330 may be provided to the bridge 300 and an output voltage $V_{out}$ 340 may be detected. The output voltage 340 may be a function of the input voltage 330, the resistance R, the resistance of the NiCr wire 320 and the resistance of the shunt resistor 350 (when the shunt resistor is coupled in parallel to the NiCr wire 320). Accordingly, a change in resistance of the NiCr wire 320 may be detected as change in output voltage $V_{out}$ 340.

It may be appreciated that ballistic impact in a fabric may involve a relatively complex phenomenon including longitudinal and/or transverse wave propagation in yarns and/or the fabric. Penetration of the fabric by the projectile may affect wave propagation and energy distribution in the fabric through, e.g., a release wave generated as a result of the penetration. A status of the fabric may depend not only on time since impact but also on a location in the fabric relative to a point of impact. The status may further depend on properties of the fabric itself, e.g., yarn material, weave, number of layers, etc. Advantageously, the present disclosure may provide a method and system for quantifying an effect of a ballistic impact based on a strain in each of a plurality of NiCr wires distributed in the fabric.

As discussed above, the resistance of NiCr wire changes with strain. Strain may be defined as a change in length divided by a nominal length:

$$\varepsilon = \frac{L - L_0}{L_0}$$

where ε is strain, L is length associated with the strain and $L_0$ is the nominal length. Strain may be provided as a percentage which is determined by multiplying the above equation by 100%.

Figure 4:
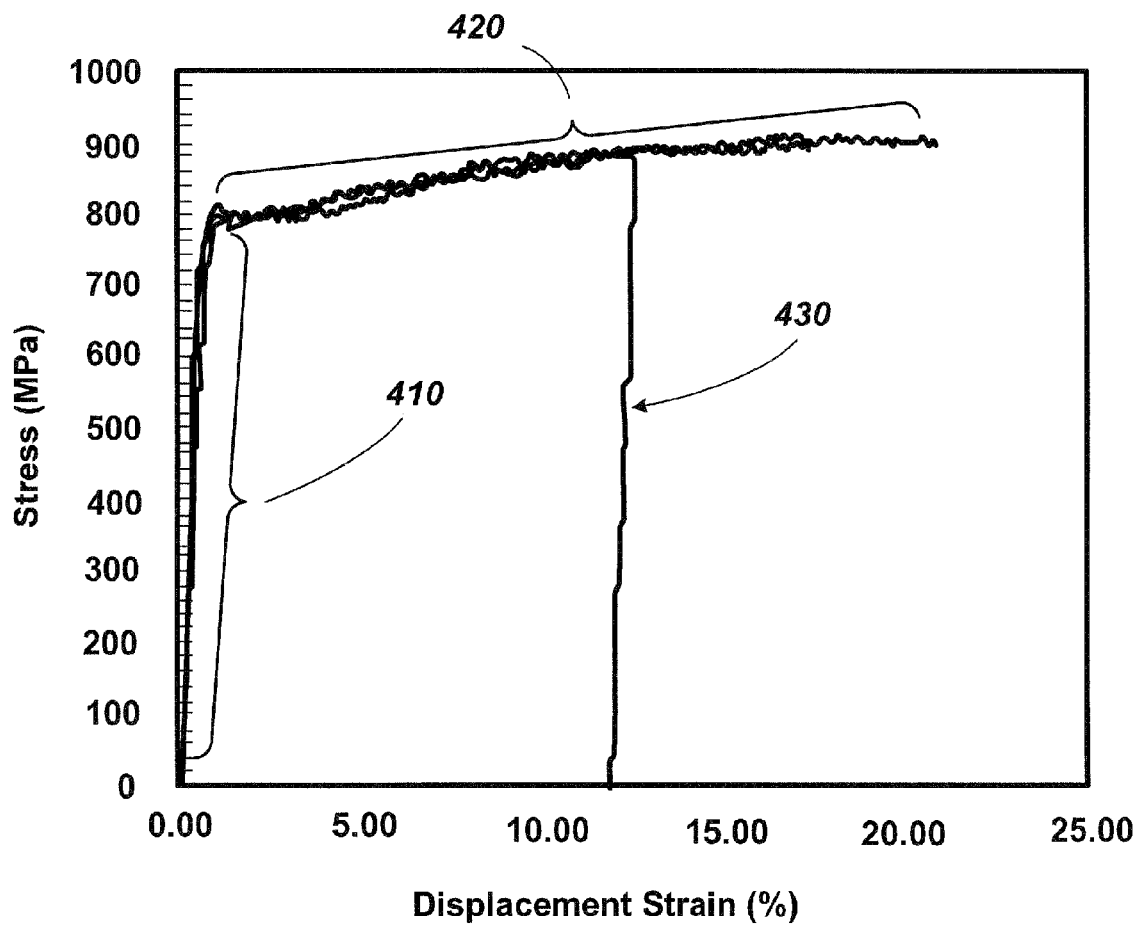
FIG. 4 depicts exemplary stress strain curves for a NiCr wire.

Strain may be generated in a wire by applying a stress or force to the wire. Stress may be understood as a force per unit area with units of Pascals. For example, a NiCr wire may be characterized by applying a force to the NiCr wire, measuring a change in length and determining strain. A stress-strain curve may then be generated, showing a relationship between stress and strain. It may be appreciated that the stress-strain relation may be elastic, plastic or failed. Elastic may be understood as a condition where the NiCr wire returns to the nominal length when the stress (force) is removed. Plastic may be understood as a condition where the NiCr wire returns to a length between the nominal length and the length associated with the force when the force is removed. Failed may be understood as broken. FIG. 4 illustrates an example of stress strain curves for a sample of NiCr wires. For example, an initial, substantially linear region 410 is elastic and lasts to a strain of about 1%. A second region 420 is plastic and lasts from strain of about 1% to about 20%. The nearly vertical line 430 at displacement strain of about 12% indicates a release of a NiCr wire, i.e., force removed, but wire length remains greater than the initial nominal length, illustrating plasticity. Failure occurred at about 20% strain.

Turning again to FIG. 2, an output of the transducer 230 may correspond to the output voltage 340 of bridge 300. A controller 240 may be coupled to the transducer 230. For example, each output of the transducer 230 may be coupled to the controller 240. In another example, a plurality of outputs of the transducer 230 may be multiplexed before being provided to the controller 240.

The controller 240 may be configured to receive the outputs from the transducer 230 and to process the outputs to determine a strain in the fabric 210. The term "controller" as used herein may include programmable hardware elements and/or a combination of hardware, software and firmware. For example, a controller may be understood as a microcontroller, e.g., including a CPU, memory (e.g., read/write and/or read-only), and/or peripherals capable of input and output. In another example, a controller may be implemented as an ASIC, i.e., a "system on a chip", or an FPGA, or the like. Accordingly, the controller 240 may include a processor 242, memory 244 and/or input/output 246. The controller 240 may be coupled to a user interface 250 and may be configured to respond to a user input from the user interface 250. The controller 240 may be coupled to a display 260 and may be configured to provide an indication of a determined strain, for example, to the display 260. In some embodiments, the controller 240 may be configured to communicate a strain and/or a status of the fabric to a remote receiver using, e.g., communication 270.

The output of transducer 230 may be a voltage based on the strain of a NiCr wire coupled to the transducer. For example, for a Wheatstone bridge, e.g., bridge 300, the output voltage may depend on a configuration of the Wheatstone bridge, including supply voltage $V_{in}$ and whether the shunt resistor $R_{sh}$ is coupled in parallel with the NiCr wire 320. Accordingly, relating strain to output voltage may be helpful. Further, the shunt resistor $R_{sh}$ may be configured to provide a measure of strain that is independent of input voltage to the bridge 300. A calibration step may be performed to determine a relation between strain and output voltage, based on the shunt resistor $R_{sh}$.

Figure 5A:
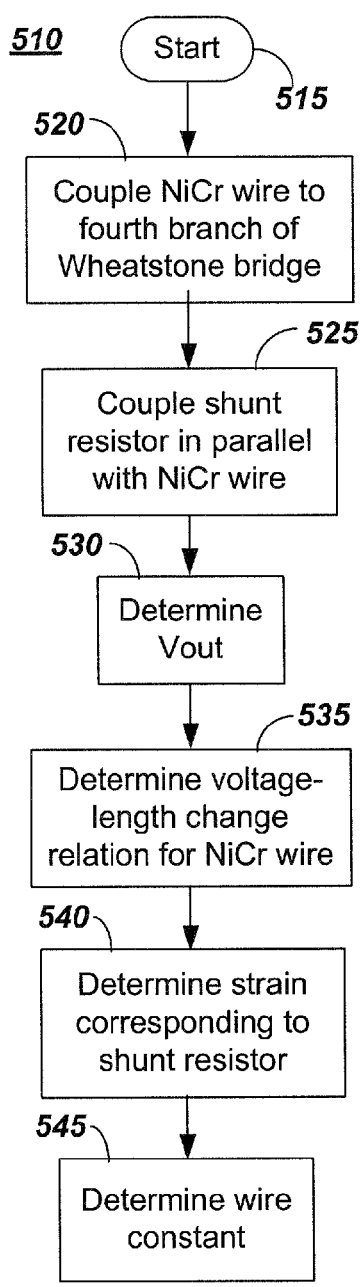
FIGS. 5A and 5B depict exemplary flow charts for calibration and strain detection including impact characterization, respectively.

Attention is directed to FIG. 5A which depicts a method 510 for calibrating a NiCr wire using a Wheatstone bridge, e.g., bridge 300. The method may begin at Start 515. The NiCr wire may be coupled 520 to the fourth branch of the Wheatstone bridge. The shunt resistor may be coupled 525 in parallel with the NiCr wire. An output voltage associated with the shunt resistor in parallel with the NiCr wire, $V_{out\text{-}shunt}$, may then be determined 530. A voltage-strain relation may then be determined 535 for the NiCr wire. The shunt resistor $R_{sh}$ may be decoupled, e.g., by opening switch 360, prior to determining the voltage strain relation. For example, a length of the NiCr wire may be increased in n steps by an incremental length, $L_i$, at each step and $V_{out}$ may be detected for each step. Each step may correspond to an incremental strain, i.e., $\Delta L$ may correspond to $\epsilon$ where $\Delta L$=step number*$L_i$. A slope of strain versus $V_{out}$, i.e., $\Delta\epsilon/\Delta V$, may be determined. Strain may be represented by each incremental change in length step. Strain corresponding to the shunt resistor may then be determined 540 based on $V_{out\text{-}shunt}$ and $\Delta\epsilon/\Delta V$, a slope of the strain-detected voltage curve.

For example, the strain corresponding to the shunt resistor may then be determined as: $\epsilon_{shunt} = V_{out\text{-}shunt} \times \Delta\epsilon/\Delta V$. For example, for R=120 ohms, nominal, $R_{sh}$=5 kilo-ohms nominal and a NiCr wire with length 50.8 cm (20 inches), with a nominal, unstrained resistance of about 121 ohms, $V_{out\text{-}shunt}$ was determined to be 1.155 volts. The same wire tested in tension yielded a slope, $\Delta\epsilon/\Delta V$, of 1.1818%/volt. Accordingly, $\epsilon_{shunt}$, the strain corresponding to the shunt resistor, for this test was: 1.155 volts*1.1818%/volt=1.365%. This test was repeated with three different NiCr wires and varying the supply voltage, Vin, to the Wheatstone bridge 300 yielding an average strain, $\epsilon_{shunt}$, corresponding to the shunt resistor of 1.414%.

A wire constant, $k_w$, with units of meter per volt may be determined 545. The wire constant may provide a relationship of strain per volt in a NiCr wire. The wire constant may be based on $\Delta\epsilon/\Delta V$, a shunt calibration factor, and may be scaled for NiCr wire length. The wire constant may provide a strain-voltage relation for an incremental length of an NiCr wire. In other words, $\epsilon_{shunt}$ may be used to determine a strain in a full length of a wire (e.g., uniform strain for full length of wire) while $k_w$ may be used to determine a strain in a portion of a NiCr wire (e.g., uniform non-zero strain in a portion of the wire and zero strain elsewhere in the wire). For example, for a shunt calibration factor, $\Delta\epsilon/\Delta V$, of 1.9921%/volt, for a NiCr wire of length 50.8 cm (20 inches), a 1 cm long wire would have a wire constant of 1.9921%/volt*50.8 cm=101.20%-cm/volt. A 1 meter length of this wire would then have a wire constant, $k_w$, of 1.012%-m/volt or 0.01012 m/volt.

Attention is directed to FIGS. 6A and 6B which depict two photographs of a fabric 600 at initial impact (FIG. 6A) of a projectile and about 15 µs after initial impact (FIG. 6B). For both figures, the projectile is traveling toward the camera. FIGS. 6A and 6B have been annotated to aid explanation. FIG. 6A illustrates a point of impact 610. The point of impact 610 is on or near a principal (primary) yarn 615. A principal (primary) yarn may be a yarn that is contacted by a projectile and/or in a path of the projectile. The fabric 600 includes a secondary yarn 620. A secondary yarn may be a yarn that is not directly contacted by a projectile but may be deformed by a primary yarn, e.g., primary yarn 615. In FIGS. 6A and 6B, the secondary yarn 620 includes a NiCr wire 625. FIGS. 6A and 6B highlight a single principal yarn 615, a single secondary yarn 620 and a single NiCr wire 635 for ease of illustration. The fabric 600 may one or more primary yarns 615, a plurality of secondary yarns 620 and a plurality of NiCr wires 625.

FIG. 6B illustrates wave propagation in the fabric 600, as a result of the impact. As illustrated in FIG. 6B, the fabric 600 has deformed into a substantially pyramid shape 630 with a peak at the impact point 610. A transverse wave 650, corresponding to a base of the pyramid may be traveling away from the impact point 610. The transverse wave 650 may deform the principal yarn 615 and the principal yarn 615 may be pulling the secondary yarn 620 and NiCr wire 625. The pull of the principal yarn 615 may deform the secondary yarn 620 and associated NiCr wire 625 which may create a longitudinal wave 640 in the secondary yarn 620 and NiCr wire 625. Accordingly, the secondary yarn 620 and NiCr wire 625 may be affected, e.g., strained, by the longitudinal wave 640 before a transverse wave 650 reaches them.

The transverse wave 650 may eventually directly affect the secondary yarn 620 and NiCr wire 625, depending on a time elapsed since impact and a distance between the point of impact 610 and the secondary yarn 620 and NiCr wire 625. A release wave may be generated if the fabric 600 is penetrated as a result of the impact. A release wave may propagate relatively more quickly than the transverse wave 640. Reflected waves may be generated at boundaries of fabric 600, primary yarn 615, secondary yarn 620 and NiCr wire 625, depending on the time elapsed since impact and a distance between the point of impact 610 and the boundaries. Accordingly, strain distribution in the yarns of a fabric (and sensing elements) may include one or more "regions", based at least in part, on time elapsed since impact and location of the yarn and/or sensing element relative to the point of impact.

Figure 7:
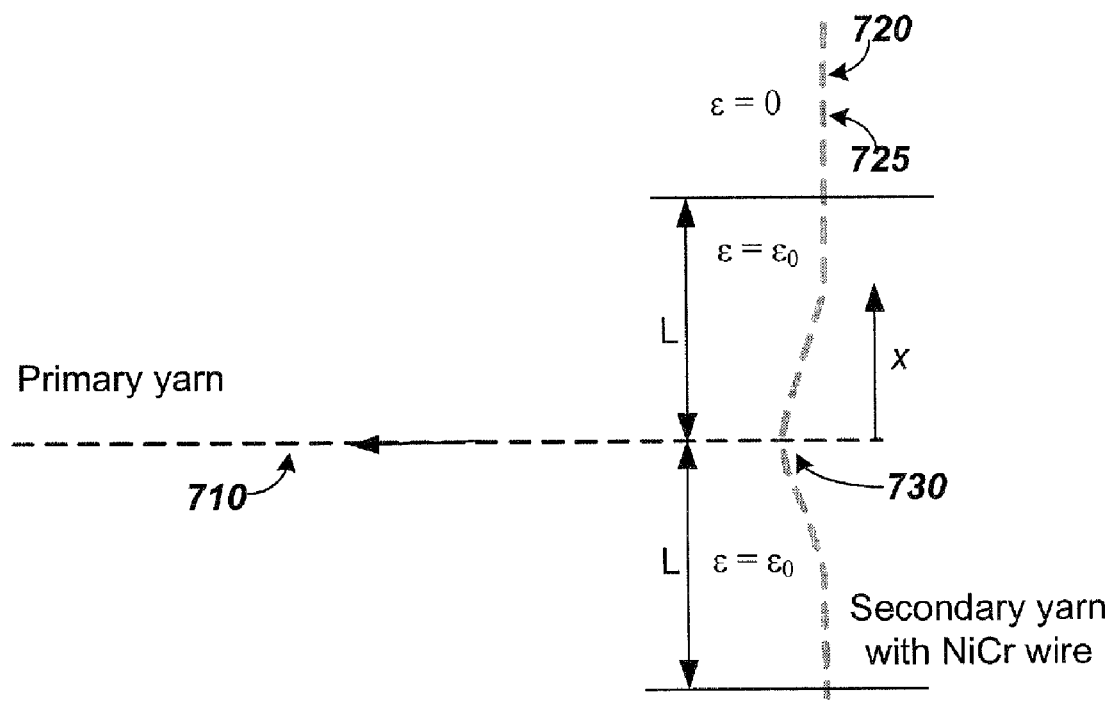
FIG. 7 depicts a sketch illustrating local strain in a NiCr wire.

For example, within a few microseconds (μs) of a ballistic impact, e.g., about 5 μs to about 30 μs, strain in a secondary yarn and NiCr wire, e.g., secondary yarn 620 and NiCr wire 625, may be "local strain". Local strain may be strain that is localized in a yarn or NiCr wire, i.e., extends less than a full length of the yarn or NiCr wire. Duration of local strain may depend, at least in part, of a speed of sound in the fabric, $c_{fab}$. Propagation velocity of the longitudinal wave may correspond to the speed of sound in the fabric. Local strain may, therefore, not be uniform along the entire length of the NiCr wire. Local strain may be described by:

$$\varepsilon(x) = k_w \frac{dV(x)}{dx}$$

where $\epsilon(x)$ is strain, x is length, $k_w$ is the wire constant, and $dV(x)/dx$ is a change in voltage with length corresponding to strain in a differential length of the NiCr wire dx. The length, x, is measured from a maximum deflection point of the NiCr wire. FIG. 7 is a sketch of a primary 710 and a secondary yarn 720, including a NiCr wire 725 with the secondary yarn 720. The secondary yarn 720 and NiCr wire 725 are experiencing a local strain caused by pull of the primary yarn 710. The primary yarn 710 and secondary yarn 720 and NiCr wire 725 intersect at a maximum deflection point 730.

A detected voltage associated with strain in the NiCr wire 725 may be determined from:

$$V(x) = \frac{1}{k_w} \int_{-L}^{+L} \varepsilon(x) dx$$

where L is a length of non-zero strain, from the maximum deflection point 730 to a region of zero strain. During local strain, propagation velocity of the longitudinal wave in the secondary yarn 720 and NiCr wire 725 may be finite. For example, as discussed above, the propagation velocity may be approximately the speed of sound in the fabric, $c_{fab}$.

It may be assumed that within the first few microseconds of local strain, e.g., about 10 μs to about 15 μs, the local strain is uniform, e.g., $\epsilon_0$, in the secondary yarn 720 and NiCr wire 725 for a length L on each side of the maximum deflection point 730. In other words, $\epsilon(-L<x<L)=\epsilon_0$ and $\epsilon(x)=0$ otherwise. It may be further assumed that the NiCr wire 725 moves with the secondary yarn 720 as if it were a fiber in the secondary yarn 720. The length L may then be defined as a function of time, t, and speed of sound in the fabric, $c_{fab}$, as $L=c_{fab}t$, therefore $\epsilon(|x|<c_{fab}t)=\epsilon_0$ and $\epsilon(|x|>c_{fab}t)=0$, where |x| means absolute value of x. Evaluating the integral above, assuming uniform strain over a distance 2L, yields:

$$V(2L) = \frac{2L\varepsilon_0}{k_w}$$

where V(2L) is the detected output voltage for the NiCr wire 725 experiencing local uniform strain $\epsilon_0$ over a length 2L. Substituting $L=c_{fab}t$ in the above equation yields:

$$V(2L) = \frac{2c_{fab}t\varepsilon_0}{k_w}$$

which may be rewritten as $V(2L)=\alpha t$ where $\alpha=2c_{fab}\epsilon_0/k_w$. It may be appreciated that α corresponds to a slope of a detected voltage versus time plot, i.e., α=dV/dt, and based on the assumptions above, α may be constant. In other words, the detected voltage versus time plot may be substantially linear. The local strain, $\epsilon_0$, may then be determined based on the slope of the detected voltage versus time plot, α, as $$\varepsilon_0 = \frac{k_w \alpha}{2c_{fab}}.$$

Accordingly, for local strain, where the strain is assumed to be uniform over a portion of the NiCr wire and zero elsewhere, the strain may be determined based on the slope of the detected voltage versus time, the wire constant and the sound speed in the fabric.

At a much later time, e.g., at a time greater than about 1000 μs after impact, strain in a NiCr wire, e.g., NiCr wire 625, may be quasi-steady state and substantially uniform over the length of the NiCr wire. In this region, strain may be considered "global", i.e., affecting an entire length of a NiCr wire. In this region, called global strain, the NiCr wire may be viewed as a strain gage in a sample under a static tensile test. In this region, strain may be determined as:

$$\varepsilon_0 = \varepsilon_{shunt} \times \frac{\Delta V_w}{\Delta V_{sh}},$$

where $\Delta V_w$ is a change in detected voltage for the NiCr wire being stretched and $\Delta V_{sh}$ is a change in detected voltage due to the shunt resistor $R_{sh}$ being coupled in parallel to the NiCr wire. The strain in the NiCr wire is assumed static over the entire length of the NiCr wire. For example, $\Delta V_w$ may be determined based on an initial $V_{out}$ associated with the NiCr wire prior to impact and a final $V_{out}$ (quasi-steady state) detected at a time greater than about 1000 μs after impact. $\Delta V_{sh}$ may be determined by detecting $V_{out}$ with and without the shunt resistor $R_{sh}$ coupled in parallel with the NiCr wire.

Figure 5B:
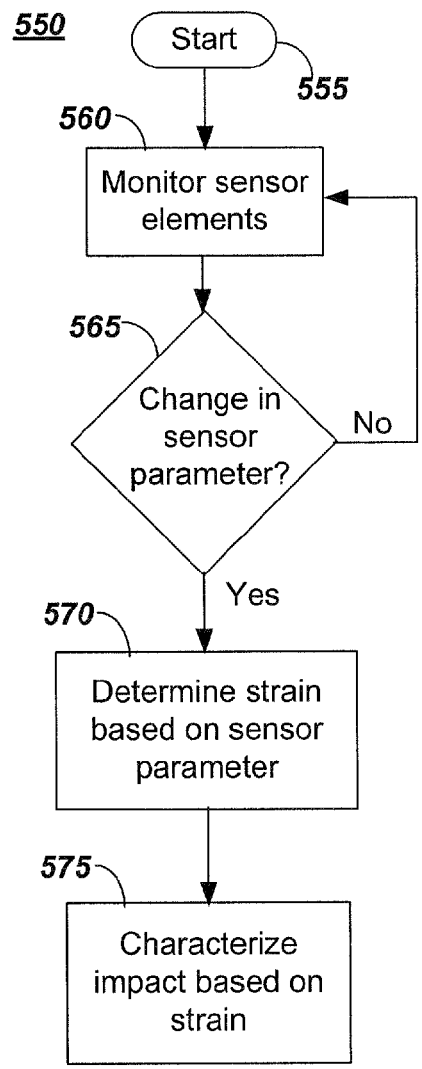

Attention is directed to FIG. 5B which depicts a flow chart 550 for characterizing an impact in a material consistent with the present disclosure. For example, system 200 may be configured to implement the method of flow chart 550. The method may begin at Start 555. One or more sensor elements may be monitored 560. For example, a sensor element may be a NiCr wire woven in a fabric. The NiCr wire may be juxtaposed with a yarn woven in the fabric. Whether a change in sensor parameter has occurred may then be determined 565. If no change in sensor parameter is detected, program flow may return to monitoring 560 the sensor elements. If a change in sensor parameter is detected, a strain based on sensor parameter may be determined 570. For example, a change in sensor parameter may be signaled by a change in output voltage of transducer 230, e.g., a Wheatstone bridge. For example, a strain, e.g., local strain, may be determined by determining a local strain based, at least in part, on a slope of a voltage versus time plot. In yet another example, a strain, e.g., a global strain may be determined based, at least in part, on a change in output voltage over time and a change in output voltage when a shunt resistor, e.g., $R_{sh}$, is coupled in parallel with a sensing element, e.g., a NiCr wire. Based on one or more strain determinations, a ballistic impact may be characterized at 575. For example, a characteristic of the ballistic impact (e.g., a location of the impact in the fabric and/or speed and/or direction of an impacting projectile) and/or a status of the fabric (e.g., strain in a yarn during impact, speed of strain waves in the fabric, whether a yarn has broken, whether one or more layers have failed, i.e., have been penetrated, and if a layer has failed, how long it took to fail) may be determined. The steps illustrated in FIG. 5B may be performed using a plurality of sensing elements, distributed throughout a fabric. Relative timing of changes in the sensor parameter among a plurality of sensing elements may provide further information regarding a characteristic of the ballistic impact and/or the status of the fabric.

Figure 8A:
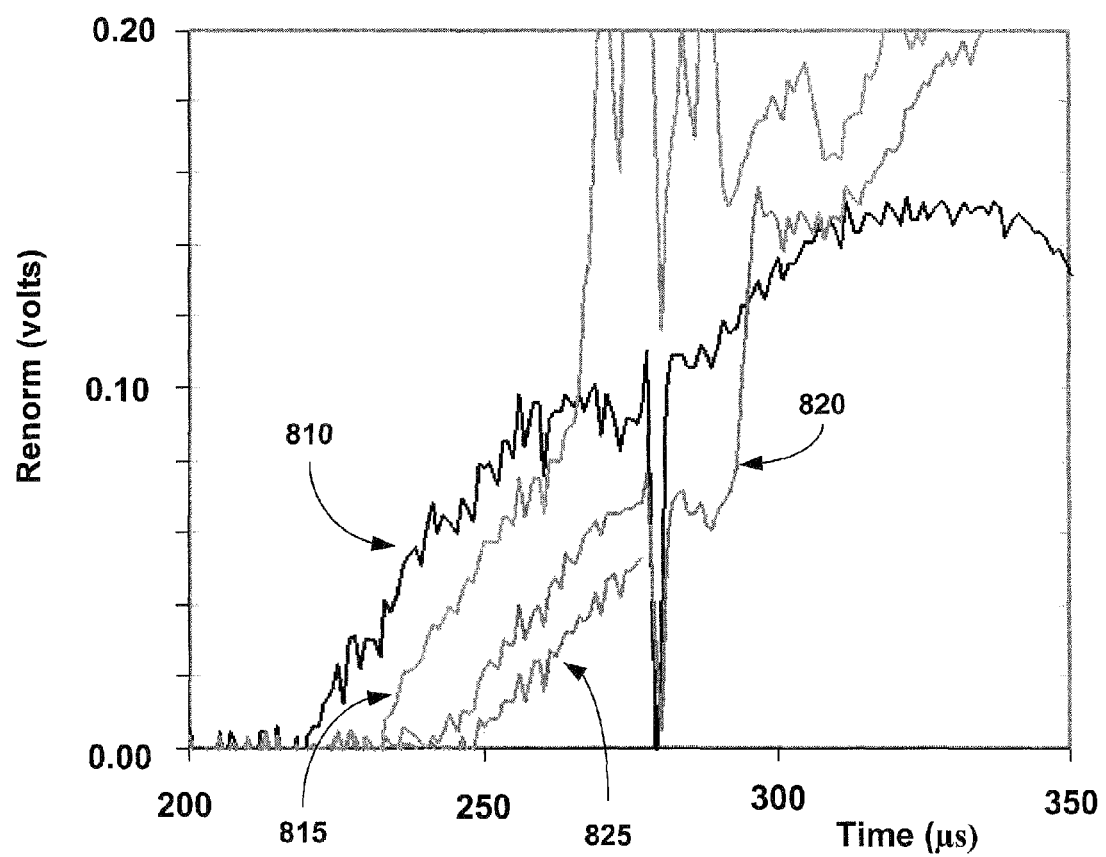
FIGS. 8A through 8C depict plots of experimental data illustrating local strain, global strain, transverse wave propagation, failure of a fabric and mixed regions.
Figure 8B:
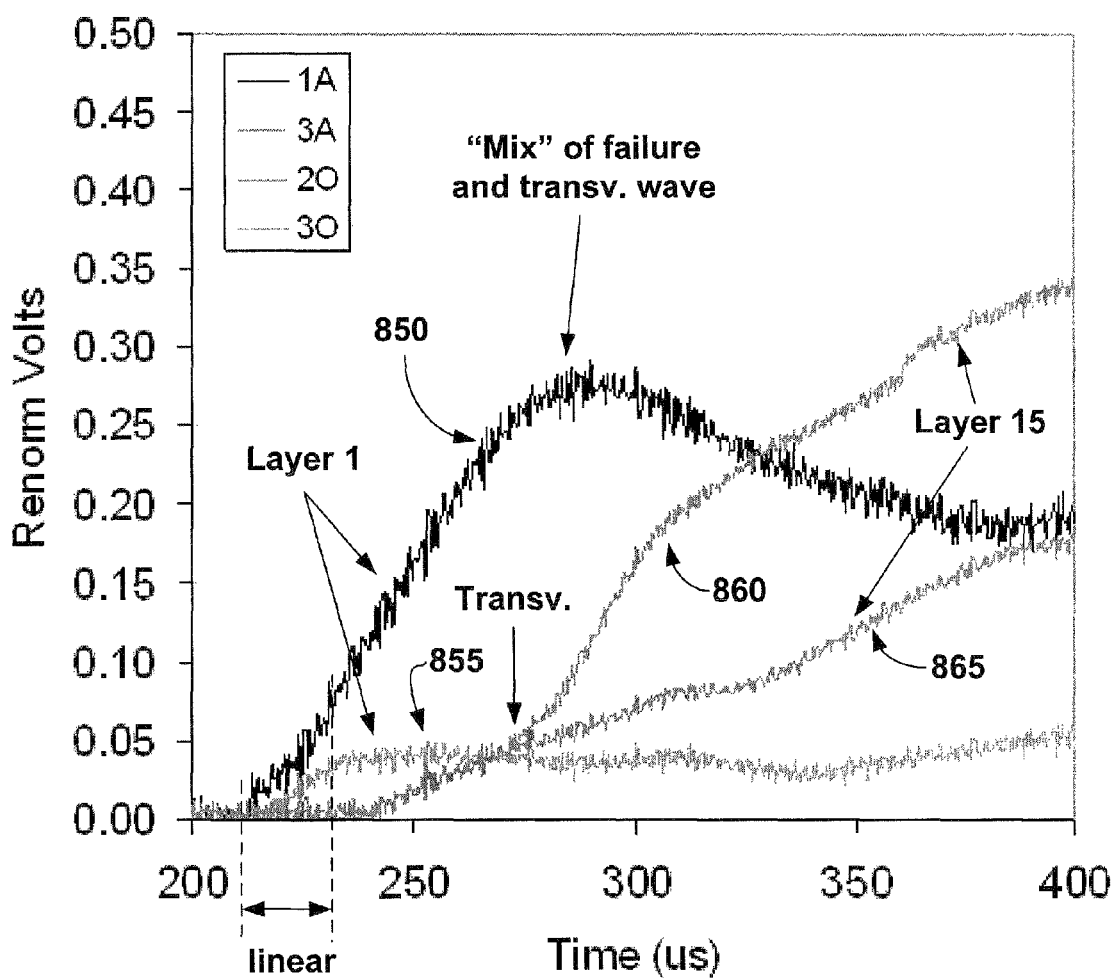
Figure 8C:
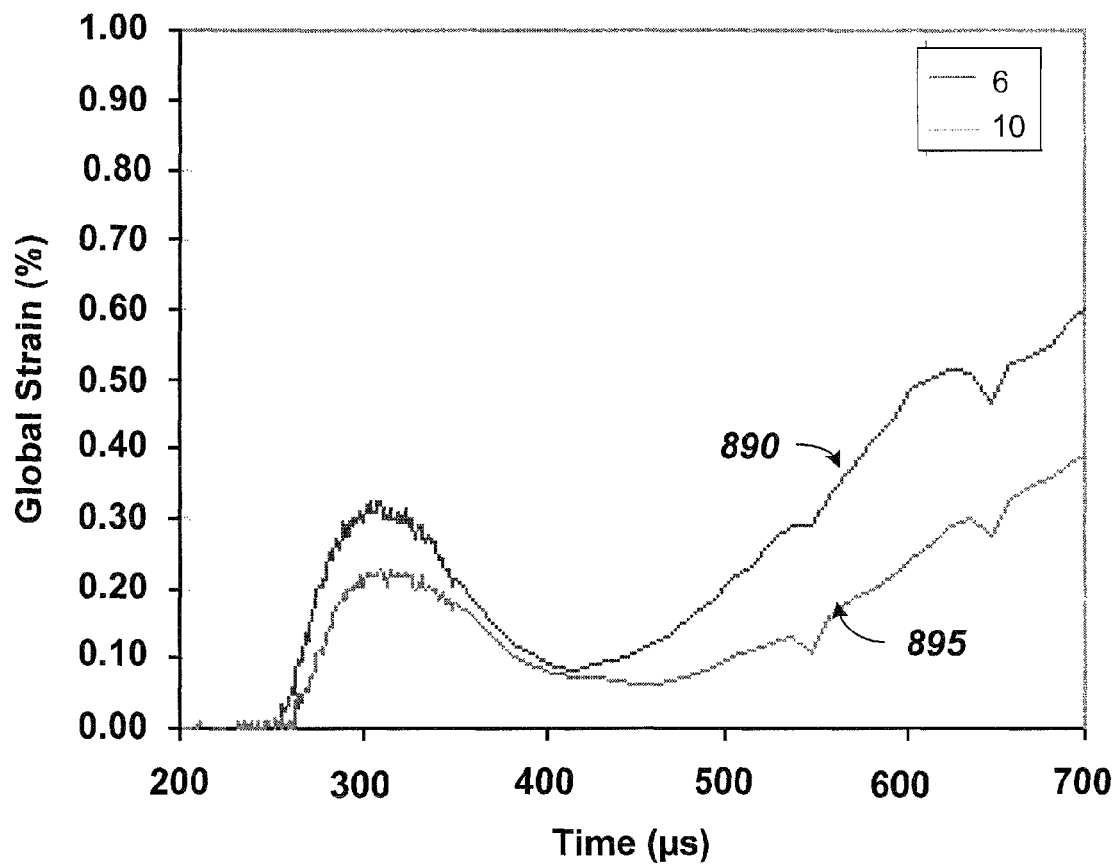

Attention is directed to FIGS. 8A through 8C that depict output signals illustrating local strain, mixed strains and/or global strains. It should be noted that for FIGS. 8A and 8B, the output voltage has been normalized to 0.5 volts. FIG. 8A depicts experimental data acquired with a system consistent with the present disclosure. FIG. 8A includes four curves corresponding to four sensing elements, e.g., NiCr wires, positioned in layers 1, 7, 15 and 22 of a fabric. The fabric may be configured such that layer 1 is the first layer impacted. Curve 810 corresponds to the sensing element in layer 1, curve 815 corresponds to the sensing element in layer 7, curve 820 corresponds to the sensing element in layer 15 and curve 825 corresponds to the sensing element in layer 22. Each of the sensing elements were placed about 2 cm from impact center. Initially, all four curves 810, 815, 820 and 825 have a substantially linear region. The durations of the substantially linear regions are approximately 20 to 30 μs. It may be appreciated that a timing of each initial increase in detected voltage for the four curves depends on the layer, e.g., layer 1, curve 810 begins to increase prior to layer 7, curve 815, etc. With reference to curve 810 (layer 1), a slope of the curve decreases beginning at approximately 325 μs. This change in slope may be a result of a release wave due to failure of the layer (which occurred only in layer 1 in this test) and a transverse wave arriving at the NiCr wire in layer 1. The local strains (in percent) determined based, at least in part, on the slopes of the initial substantially linear regions, using the equation for local strain above, were 0.39 for layer 1, 0.37 for layer 7, 0.31 for layer 15 and 0.25 for layer 22.

FIG. 8B includes four curves. Curves 850 and 855 correspond to NiCr wires located 1 cm and 3 cm, respectively, from impact center, in layer 1 of a fabric. Curves 860 and 865 correspond to NiCr wires located 2 cm and 3 cm, respectively, from impact center in layer 15 of the fabric. Similar to the curves depicted in FIG. 8A, the curves in FIG. 8B include an initial substantially linear region of local strain. Arrival of a transverse wave and/or failure of a layer may be indicated by a deviation from the linearity of the initial substantially linear region. The particular deviation may depend on a location of a sensing element relative to the impact point. For example, if the sensing element is relatively close to the impact point, the transverse wave may cross the NiCr wire relatively early and the strain may increase sharply. This case may be indicated by an increase in slope of the voltage versus time curve as shown, for example, in curve 850, e.g., between about 225 μs and about 250 μs. If the NiCr wire is relatively distant from the impact point then the transverse wave may cross the NiCr wire at a relatively later time as shown, for example, in curves 860 and 865.

For the experimental data of FIG. 8B, only layer 1 was penetrated. Similar to FIG. 8A, penetration, i.e., failure of a layer, is indicated by a reduction in slope from the initial, local strain region. If penetration occurs, it may release the strain. It may be appreciated that a release wave travels relatively more quickly than a transverse wave. For NiCr wires relatively close to the impact point, both the transverse wave and the release wave may "mix" as illustrated by curve 850.

For NiCr wires relatively distant from the impact point, the release wave may arrive before the transverse wave resulting in a decrease in slope. The transverse wave may then increase the slope as shown, for example, in curves 890 and 895. Curves 890 and 895 correspond to NiCr wires in layer 1, positioned 6 cm and 10 cm, respectively, from impact center. For example, for curve 890, the transverse wave begins to increase the slope of global strain curve at about 420 μs, approximately 180 μs after impact. It may be appreciated that the curves in FIG. 8C illustrate global strain in percent.

As FIGS. 8A through 8C illustrate, in addition to the initial, local strain region and the relatively later, quasi-steady state global strain region, a transverse wave and/or release wave may affect the detected voltage waveforms that correspond to strain in the sensing elements. The effects on the voltage waveforms may depend on the distance between the sensing elements and the impact point. Between the initial local strain region and the quasi-steady state global strain region, there may be a mixed region of complex wave interaction. In this region, reflected waves from edges of the fabric, release waves from penetration and/or transverse waves may mix. Detected voltage waveforms in this region are generally complex and somewhat difficult to interpret. Duration of the mixed region may be up to about 1000 μs.

It is contemplated that a system consistent with the present disclosure, e.g., system 200, may be configured to determine a parameter associated with a ballistic impact based on the strain detected in one or more sensing elements. For example, the parameter may be a direction and/or speed of a projectile prior to the impact. In another example, the parameter may be a "signature" (strain reading or percent deformation of the sensing element, duration of strain, change in strain over time or dε/dt) that may be used to identify the cause of the ballistic impact, e.g., projectile type such as projectile caliber or type of projectile (e.g., hollow or solid point). Based on these parameters, e.g., projectile type and speed and/or a flight distance from a standard gun muzzle may be determined.

The system 200 may be used in a battlefield situation, for example, to detect a ballistic impact and to determine a status of a fabric as a result of the ballistic impact. For example, status of the fabric may include diagnostics of a layer, e.g., strain in a yarn during impact, speed of strain waves in the fabric, whether a yarn has broken, whether one or more layers have failed, i.e., have been penetrated, and if a layer has failed, how long it took to fail. The system 200 may be further configured to communicate characteristics and/or parameters of the ballistic impact and/or the status of the fabric, remotely and automatically using, for example, communication 270.

It is contemplated that the system 200 may be used with controllable fabric such as rheological fabric configured to react to a detected ballistic impact. For example, the controllable fabric may be configured to increase its rigidity (e.g., tensile modulus) based on the detected ballistic impact. For example, the controllable fabric may be an electro-rheological fabric whose rigidity may be controlled through application of an electric field. In another example, a protective mechanism for humans and/or buildings may be triggered based on detection of a ballistic impact.

It is further contemplated that the system 200 may be used in experimentation to validate models and to help understand penetration mechanics associated with a fabric.

Figure 9:
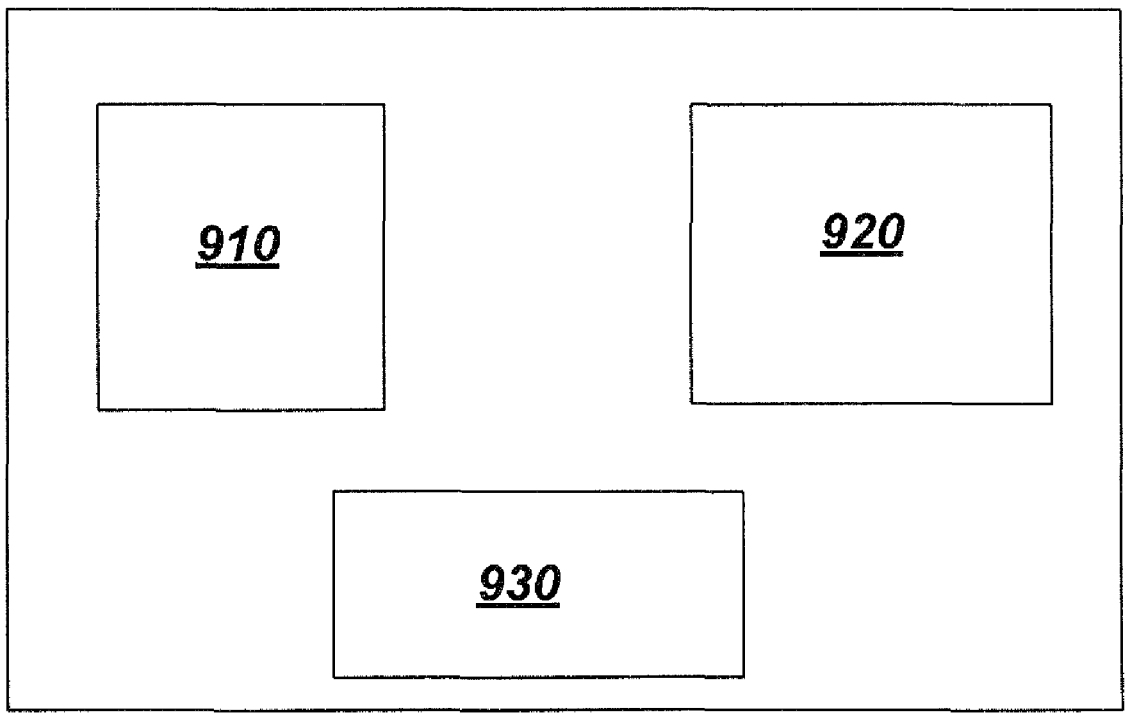
FIG. 9 illustrates an example of a strain detection system that contains a processor, machine readable media and a user interface.

It should also be appreciated that the functionality described herein for the embodiments of the present invention may be implemented by using hardware, software, or a combination of hardware and software, as desired. If implemented by software, a processor and a machine readable medium are required. The processor may be any type of processor capable of providing the speed and functionality required by the embodiments of the invention. Machine-readable memory includes any media capable of storing instructions adapted to be executed by a processor. Some examples of such memory include, but are not limited to, read-only memory (ROM), random-access memory (RAM), programmable ROM (PROM), erasable programmable ROM (EPROM), electronically erasable programmable ROM (EEPROM), dynamic RAM (DRAM), magnetic disk (e.g., floppy disk and hard drive), optical disk (e.g., CD-ROM), and any other device that can store digital information. The instructions may be stored on a medium in either a compressed and/or encrypted format. Accordingly, in the broad context of the present invention, and with attention to FIG. 9, a strain detection system may include a processor (910) and machine readable media (920) and user interface (930).

Although illustrative embodiments and methods have been shown and described, a wide range of modifications, changes, and substitutions is contemplated in the foregoing disclosure and in some instances some features of the embodiments or steps of the method may be employed without a corresponding use of other features or steps. Accordingly, it is appropriate that the claims be construed broadly and in a manner consistent with the scope of the embodiments disclosed herein.

What is claimed is:

1. A system for characterizing an impact in a fabric, said system comprising:
a fabric comprising a plurality of individual yarns that have been woven into a plurality of layers wherein said fabric includes a sensing element woven in each of said layers to provide a plurality of sensing elements;
wherein a parameter of said plurality of sensing elements depends on a strain in said sensing element in each of said fabric layers;
a transducer coupled to each of said sensing element wherein said transducer is configured to generate an output voltage versus time including an initial linear slope region based on said parameter of said sensing, wherein said initial linear slope region is related to said strain according to the equation $\epsilon = k_w \alpha / 2c_{fab}$, where $\epsilon$ is said strain, $k_w$ is a wire constant associated with said sensing element, $\alpha$ is said linear slope and $c_{fab}$ is the speed of sound in said fabric, and wherein said strain is a local strain such that said local strain is uniform over a portion of said sensing element; and a controller coupled to said transducer, said controller configured to receive said output of said transducer, to determine a strain in said sensing element based, at least in part, on a change in said output voltage versus time of said transducer for each of said fabric layers, and to characterize said impact in said fabric based on said strain in said sensing element by determination of the location of said impact and failure of a layer indicated by a deviation from the linearity of said initial linear region of said voltage versus time slope.

2. The system of claim 1 wherein said sensing element is a NiCr wire.

3. The system of claim 1 wherein said transducer is a full Wheatstone bridge.

4. The system of claim 1 further comprising a shunt resistor controllably coupled in parallel with said sensing element wherein said shunt resistor is configured to provide said output of said transducer independent of a supply voltage to said transducer.

5. The system of claim 1 further comprising a communication element configured to transmit a signal based on said strain in said sensing element to a remote receiver.

6. The system of claim 1 comprising a plurality of sensing elements distributed in said fabric.

7. The system of claim 6 comprising a plurality of transducers wherein each transducer is coupled to at least one of said plurality of sensing elements, said controller is coupled to each of said plurality of transducers and said controller is configured to characterize said impact based on a plurality of outputs from said transducers.

8. The system of claim 1 wherein said fabric has a tensile strength of equal to or greater than 500,000 psi.

9. The system of claim 1 wherein said controller is configured to characterize said impact by further determining one or more of the following: a speed of an impacting projectile and/or a direction of said impacting projectile.

10. The system of claim 1 wherein said controller is configured to characterize said impact by determining one or more of a strain reading, a percent deformation of said sensing element, a duration of said strain, and/or a change in said strain over time ($d\epsilon/dt$) associated with said impact.

11. The system of claim 1 wherein said controller is configured to further characterize said impact by determining one or more of a strain in a yarn during impact, a speed of a strain wave in said fabric, whether a yarn has broken and if said layer has failed, a time from impact to failure of said layer.

12. A method for characterizing an impact in a fabric, said method comprising:
providing a fabric comprising a plurality of individual yarns that have been woven into a plurality of layers wherein said fabric includes a sensing element woven into each of said layers;
monitoring an output, said output based on a parameter of said plurality of sensing elements wherein said parameter of said sensing element depends on a strain in said sensing element and said output comprises voltage versus time including an initial linear slope region, wherein said initial linear slope region is related to said strain according to the equation $\epsilon = k_w \alpha / 2c_{fab}$, where $\epsilon$ is said strain, $k_w$ is a wire constant associated with said sensing element, $\alpha$ is said linear slope and $c_{fab}$ is the speed of sound in said fabric, and wherein said strain is a local strain such that said local strain is uniform over a portion of said sensing element;
detecting a change in said output;
determining said strain in said sensing element based on said change in said output; and characterizing said impact in said fabric based on said strain in said sensing element and determining the location of said impact and failure of a layer indicated by a deviation from the linearity of said initial portion of said voltage versus time slope.

13. The method of claim 12 wherein said sensing element is NiCr wire and said parameter is resistance.

14. The method of claim 13 wherein said output is a voltage generated by a Wheatstone bridge comprising said NiCr wire.

15. The method of claim 12 further comprising calibrating said output.

16. The method of claim 14 wherein said determining said strain in said sensing element comprises determining a local strain based on a change in said output voltage over time, a wire constant and a sound speed in said fabric.

17. The method of claim 12 wherein said determining said strain in said sensing element comprises determining a global strain based, at least in part, on a change in said output.

18. The method of claim 12 wherein said characterizing said impact comprises determining a speed of an impacting projectile and/or a direction of said impacting projectile.

19. The method of claim 12 wherein said characterizing said impact comprises determining one or more of a strain reading, a percent deformation of said sensing element, a duration of said strain, and/or a change in said strain over time ($d\epsilon/dt$) associated with said impact.

20. The method of claim 12 wherein said characterizing said impact comprises:
determining one or more of a strain in a yarn during impact, a speed of a strain wave in said fabric, whether a yarn has broken, and if said layer has failed, a time from impact to failure of said layer.

21. The method of claim 12 further comprising increasing a tensile modulus of said fabric based on said strain.

22. The method of claim 12 wherein said fabric has a tensile strength of equal to or greater than 500,000 psi.

23. An article comprising a storage medium having stored thereon instructions that when executed by a machine result in the following operations:
monitoring an output, said output based on a parameter of a sensing element wherein said sensing element is woven in a fabric comprising a plurality of individual yarns that have been woven into a plurality of layers wherein said fabric includes a sensing element woven in each of said layers and said parameter of said sensing element depends on a strain in said sensing element and said output comprises voltage versus time including an initial slope region, wherein said initial linear slope region is related to said strain according to the equation $\epsilon = k_w \alpha / 2 c_{fab}$, where $\epsilon$ is said strain, $k_w$ is a wire constant associated with said sensing element, $\alpha$ is said linear slope and $c_{fab}$ is the speed of sound in said fabric, and wherein said strain is a local strain such that said local strain is uniform over a portion of said sensing element;
detecting a change in said output;
determining said strain in said sensing element based on said change in said output; and
characterizing an impact in said fabric based on said strain in said sensing element and determining the location of said impact and failure of a layer indicated by a deviation from the linearity of said initial portion of said voltage versus time slope.

24. The article of claim 23 wherein said instructions further result in the following operations:
calibrating said output.

25. The article of claim 23 wherein said determining said strain in said sensing element comprises:
determining a local strain based on a change in said output voltage over time, a wire constant and a sound speed in said fabric.

26. The article of claim 23 wherein said determining said strain in said sensing element comprises:
determining a global strain based, at least in part, on a change in said output.

27. The article of claim 23 wherein said characterizing said impact comprises:
determining a speed of an impacting projectile and/or a direction of said impacting projectile.

28. The article of claim 23 wherein said characterizing said impact comprises:
determining one or more of a strain reading, a percent deformation of said sensing element, a duration of said strain, and/or a change in said strain over time ($d\epsilon/dt$) associated with said impact.

29. The article of claim 23 wherein said characterizing said impact comprises:
determining one or more of a strain in a yarn during impact, a speed of a strain wave in said fabric, whether a yarn has broken and if said layer has failed, a time from impact to failure of said layer.

* * * * *